United States Patent
Son et al.

(10) Patent No.: US 11,406,950 B2
(45) Date of Patent: Aug. 9, 2022

(54) BUBBLE VOLUME CONTROL METHOD AND BUBBLE VOLUME CONTROLLING APPARATUS

(71) Applicant: SOGANG UNIVERSITY RESEARCH FOUNDATION, Seoul (KR)

(72) Inventors: Gihun Son, Seoul (KR); Jaewon Lee, Seoul (KR)

(73) Assignee: SOGANG UNIVERSITY RESEARCH FOUNDATION, Seoul (KR)

(*) Notice: Subject to any disclaimer, the term of this patent is extended or adjusted under 35 U.S.C. 154(b) by 783 days.

(21) Appl. No.: 16/342,973

(22) PCT Filed: Mar. 6, 2018

(86) PCT No.: PCT/KR2018/002736
§ 371 (c)(1),
(2) Date: Apr. 18, 2019

(87) PCT Pub. No.: WO2018/164493
PCT Pub. Date: Sep. 13, 2018

(65) Prior Publication Data
US 2020/0055013 A1    Feb. 20, 2020

(30) Foreign Application Priority Data
Mar. 10, 2017    (KR) .................. 10-2017-0030614

(51) Int. Cl.
*B01F 31/80*    (2022.01)
*B06B 1/02*    (2006.01)
(Continued)

(52) U.S. Cl.
CPC ............ *B01F 31/89* (2022.01); *B01F 23/238* (2022.01); *B06B 1/02* (2013.01); *B01F 2101/2202* (2022.01)

(58) Field of Classification Search
CPC   B01F 31/89; B01F 23/238; B01F 2101/2202; B01F 31/86; B01F 33/30;
(Continued)

(56) References Cited

U.S. PATENT DOCUMENTS

2020/0055013 A1*  2/2020  Son .................... B01F 33/30

FOREIGN PATENT DOCUMENTS

JP       2003-265939 A      9/2003
JP       2006-289183 A     10/2006
(Continued)

OTHER PUBLICATIONS

International Search Report in International Application No. PCT/KR2018/002736, dated Jun. 21, 2018 with English translation, 5pages.

*Primary Examiner* — Daniel Pihulic
(74) *Attorney, Agent, or Firm* — Park, Kim & Suh, LLC

(57) ABSTRACT

Provided is a bubble volume control method and apparatus, and more particularly, to a bubble volume control method and apparatus for controlling the volume of a bubble by increasing or decreasing the volume of the bubble by emitting an ultrasonic wave having a resonance frequency corresponding to the size of the bubble located at the bottom of a container containing a liquid, such as water with bubbles composed of air, vapor, etc., toward the bubble by using an ultrasonic generator above the container, and maximizing a function of adjusting the volume of a bubble through a resonance effect by adjusting a liquid surface height of a liquid with the bubble according to a wavelength of an emitted ultrasonic wave.

16 Claims, 4 Drawing Sheets

(51) Int. Cl.
*B01F 23/23* (2022.01)
*B01F 101/00* (2022.01)

(58) Field of Classification Search
CPC ...... B01F 33/403; B01F 35/3201; B06B 1/02;
A61B 17/22; A61B 2017/22088; A61K
9/00; A61K 41/00; A61K 9/0009; A61K
41/13; A61N 7/00
See application file for complete search history.

(56) References Cited

FOREIGN PATENT DOCUMENTS

| | | | | |
|---|---|---|---|---|
| JP | 2011-078894 A | 4/2011 | | |
| JP | 2014-050817 A | 3/2014 | | |
| JP | 2014-198327 A | 10/2014 | | |
| KR | 10-2016-0099794 A | 8/2016 | | |
| WO | WO-2015141917 A1 * | 9/2015 | ......... | A61K 47/6925 |
| WO | WO-2018164493 A1 * | 9/2018 | ............. | A61B 17/22 |
| WO | WO-2019004669 A3 * | 2/2019 | ............. | A61K 41/00 |
| WO | WO-2019156477 A1 * | 8/2019 | ....... | A61B 17/12195 |
| WO | WO-2019235717 A1 * | 12/2019 | .......... | B01F 11/0266 |

* cited by examiner

# BUBBLE VOLUME CONTROL METHOD AND BUBBLE VOLUME CONTROLLING APPARATUS

CROSS-REFERENCE TO RELATED APPLICATIONS

This application is the National Stage filing under 35 U.S.C. 371 of International Application No. PCT/KR2018/002736, filed on Mar. 6, 2018, which claims the benefit of Korean Patent Application No. 10-2017-0030614, filed on Mar. 10, 2017, the contents of which are all hereby incorporated by reference herein in their entirety.

TECHNICAL FIELD

The present invention relates to a bubble volume control method and apparatus, and more particularly, to a bubble volume control method and apparatus for controlling the volume of a bubble by increasing or decreasing the volume of the bubble by emitting an ultrasonic wave having a resonance frequency corresponding to the size of the bubble located at the bottom of a container containing a liquid, such as water with bubbles composed of air, vapor, etc., toward the bubble by using an ultrasonic generator above the container, and maximizing a function of adjusting the volume of a bubble through a resonance effect by adjusting a liquid surface height of a liquid with the bubble according to a wavelength of an emitted ultrasonic wave.

BACKGROUND ART

The present invention relates to a bubble volume control method and apparatus for controlling the volume of a bubble by increasing or decreasing the volume of the bubble by emitting an ultrasonic wave having a resonance frequency corresponding to the size of the bubble located at a wall surface of a container containing a liquid, such as water with bubbles composed of air, vapor, etc., toward the bubble by using an ultrasonic generator above the container, and maximizing a function of adjusting the volume of a bubble through a resonance effect by adjusting a liquid surface height of a liquid with the bubble according to a wavelength of an ultrasonic wave.

Recently, the behavior of a bubble in an ultrasonic region has been applied and studied not only in the field of medical diagnosis and operations, including in vitro lithotripsy and selective medicine delivery, but also in chemical mixing technology, ultrasonic cleaning, cavitation, etc. conducted in a lab-on-a-chip (LOC) device.

Many attempts have been made to try to apply existing studies on the behavior of a bubble in an ultrasonic region to various fields.

As concrete examples, the existing studies apply to ultrasonography using bubbles of a contrast medium in a blood vessel having a diameter of several μm or research has been conducted on a technique for necrotizing or blocking cells, e.g., cancer cells, and substances harmful to the body by blocking blood flow by growing the size of bubbles in a blood vessel to block the blood vessel. Furthermore, there have been attempts to apply the existing studies to a technique for delivering medicine by injecting a bubble containing particles of the medicine into the body and popping the bubble near tissue requiring treatment by pressurizing the bubble using an ultrasonic wave.

As described above, a technique for controlling a bubble using an ultrasonic wave has been applied and studied in relation to techniques such as chemical mixing, ultrasonic cleaning, cavitation, etc. conducted in a Lab-on-a-chip (LOC) device, as well as medical applications.

However, techniques for removing or creating bubbles in a liquid have been accumulated to a certain extent but research on a technique for adjusting the volume of a bubble in a liquid to a desired size by precisely increasing or decreasing the volume of the bubble is urgently needed.

DETAILED DESCRIPTION OF THE INVENTION

Technical Problem

The present invention is directed to a bubble volume control method and apparatus for controlling the volume of a bubble by increasing or decreasing the volume of the bubble by emitting an ultrasonic wave onto a container containing a liquid toward the bubble, and maximizing a function of adjusting the volume of a bubble through a resonance effect by adjusting a liquid surface height of a liquid containing the bubble according to a wavelength of an ultrasonic wave.

Technical Solution

According to an aspect of the present invention, there is provided a bubble volume control method comprising, when there is a bubble of a radius R at the bottom of a container containing a liquid of a density p and a specific heat ratio γ, controlling volume of the bubble to be reduced by emitting an ultrasonic wave having a resonance frequency $f_N$ toward the bubble through an ultrasonic generator provided above a surface of the liquid to pressurize the bubble, wherein the resonance frequency $f_N$ is defined by:

$$f_N = \frac{1}{2\pi}\sqrt{\frac{1}{\rho R^2}\left[3\gamma p_o + 2(3\gamma - 1)\frac{\sigma}{R}\right]},$$

wherein p represents the density of the liquid contained in the container, R represents the radius of the bubble, Po represents an atmospheric pressure, and σ represents surface tension of the liquid.

And the ultrasonic generator may pressurize the bubble by transmitting a pressure wave Ps of a sinusoidal shape to the bubble through the liquid as a medium, and the pressure wave Ps may be defined by:

$$Ps = P + a^*\sin(2\pi^* f^* t),$$

wherein a represents an amplitude of the ultrasonic wave, f represents a frequency of the ultrasonic wave, and t represents time.

And the bubble may be located at the bottom of the container, and a height H from the bubble to the surface of the liquid is ¼ of a wavelength Λ of the ultrasonic wave.

And the ultrasonic generator may transmit a pressure wave Ps of a sinusoidal shape to the bubble.

And the bubble may be located at the bottom of the container, and a height H from the bubble to the surface of the liquid is ½ of a wavelength Λ of the ultrasonic wave.

And when an operation of the ultrasonic generator is stopped, pressure applied to the bubble may be removed and thus the volume of the bubble is restored to its original volume.

And the volume of the bubble may be controlled to be within a predetermined range by repeating an operation period in which the ultrasonic generator is operated and a non-operation period in which the operation of the ultrasonic generator is stopped.

And the radius of the bubble of which the volume may be controlled by the ultrasonic wave generated by the ultrasonic generator is in a range of 1 μm to 100 μm.

And a pressure of an amplitude of the pressure wave Ps may be in a range of 1.013 kPa to 10.13 kPa.

And the resonance frequency $f_N$ may be in a range of 33 kHz to 4745 kHz.

And the height H of the surface of the liquid may be in a range of 81 μm to 11647 μm.

And the radius of the bubble may be inversely proportional to the resonance frequency $f_N$ of the ultrasonic wave generated by the ultrasonic generator, and may be proportional to the height H of the surface of the liquid.

And a according to an aspect of the present invention, there is provided a bubble volume control apparatus comprising an ultrasonic generator and a liquid container, wherein a liquid of a density p and a specific heat ratio γ is contained in the liquid container, the ultrasonic generator emits an ultrasonic wave toward a surface of the liquid in the liquid container, and when a radius of a bubble at the bottom of the liquid container is R, the ultrasonic generator may generate an ultrasonic wave having a resonance frequency $f_N$ to pressurize the bubble to reduce the volume of the bubble, wherein the resonance frequency is defined by:

$$f_N = \frac{1}{2\pi}\sqrt{\frac{1}{\rho R^2}\left[3\gamma p_o + 2(3\gamma - 1)\frac{\sigma}{R}\right]},$$

wherein p represents the density of the liquid contained in the container, R represents the radius of the bubble, Po represents an atmospheric pressure, and σ represents surface tension of the liquid.

And the ultrasonic wave generated by the ultrasonic generator may comprise a plane wave of a sinusoidal shape, and a liquid surface height of the liquid contained in the liquid container is ¼ of a wavelength λ of the ultrasonic wave having the resonance frequency $f_N$ and generated by the ultrasonic generator from the bottom of the liquid container.

Advantageous Effects

According to a bubble volume control method and apparatus according to the present invention, when an ultrasonic wave having a resonance frequency corresponding to the size of a bubble located at the bottom of a container is emitted to a surface of water having a height that is in a certain ratio with the wavelength of the ultrasonic wave, the amount of pressure to be applied to a point at which the bubble is located may be controlled by resonance produced by the ultrasonic wave and the bubble and multiple resonance produced when the resonance is amplified through an effect of the height of the container achieved by taking into account a wavelength corresponding to a largest amplitude, thereby controlling the behavior, e.g., growth, contraction, or removal, of the bubble by changing the pressure.

Furthermore, an effect of compressing a liquid by growing, contracting, or removing the bubble as described above is increased as an angle of contact between the bubble and the bottom of the container becomes smaller.

MODE OF THE INVENTION

Hereinafter, exemplary embodiments of the present invention will be described in detail. The present invention is, however, not limited thereto and may be embodied in many different forms. Rather, the embodiments set forth herein are provided so that this disclosure will be thorough and complete, and fully convey the scope of the invention to those of ordinary skilled in the art. Throughout the specification, the same reference numbers represent the same elements.

Figure 1:
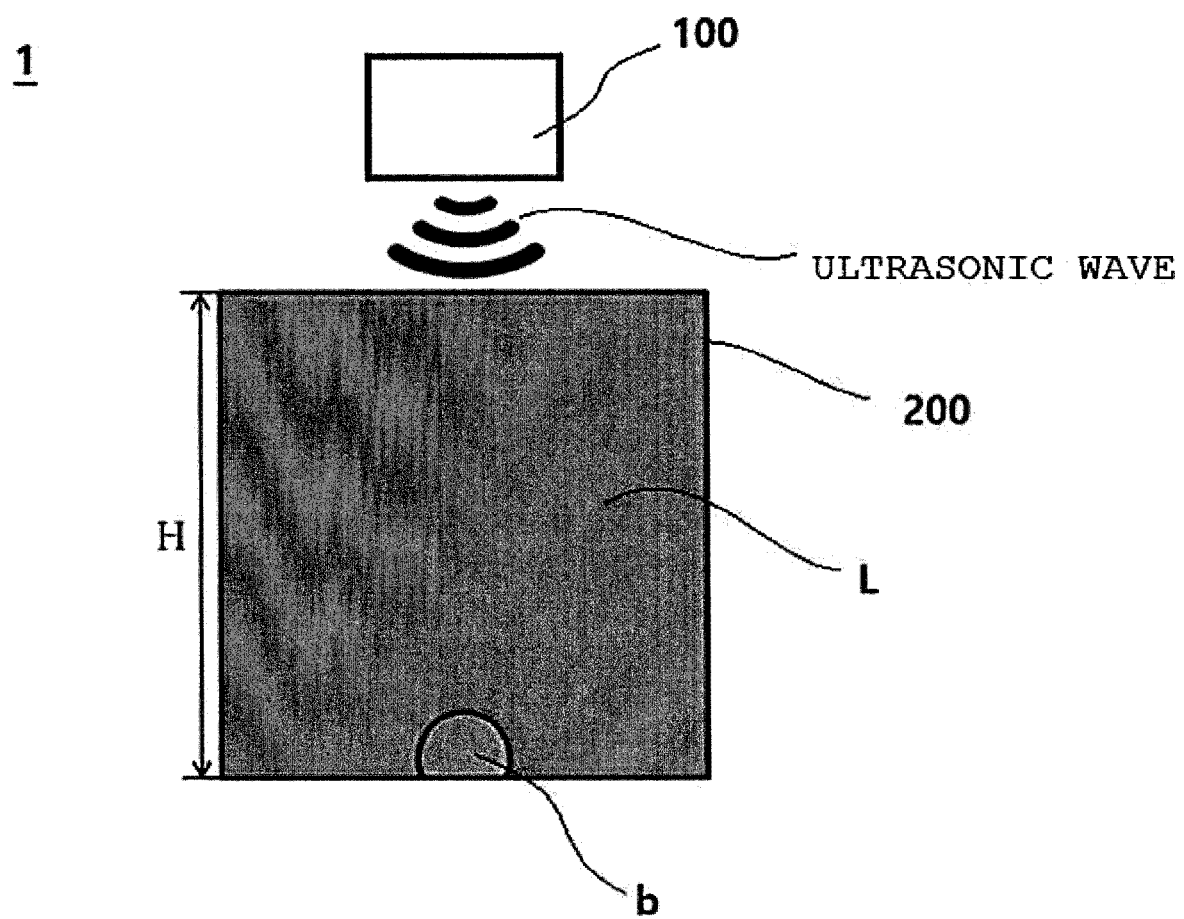
FIG. 1 is a diagram illustrating the structure of a bubble volume control apparatus employed in a bubble volume control method, according to the present invention.

FIG. 1 is a diagram illustrating the structure of a bubble volume control apparatus 1 employed in a bubble volume control method, according to the present invention.

The present invention provides a bubble volume control method of controlling the volume of a bubble b having a radius R to be reduced by applying pressure to the bubble b by emitting an ultrasonic wave having a resonance frequency $f_N$ defined below toward the bubble b under an atmospheric pressure of Po by an ultrasonic generator 100 provided above a surface of the liquid, when the bubble b is located at the bottom of a container 200 containing a liquid of a density of P, a specific heat ratio of γ, and a surface tension of a; and a bubble volume control apparatus employing the same.

The bubble volume control apparatus 1 according to the present invention generates a bubble b composed of a gas such as fine air at a surface of an inner wall (particularly, a bottom) of the container 200 containing a liquid such as water. The resonance frequency $f_N$ of the bubble b is determined according to a radius R of the generated bubble b by using the following equation:

$$f_N = \frac{1}{2\pi}\sqrt{\frac{1}{\rho R^2}\left[3\gamma p_o + 2(3\gamma - 1)\frac{\sigma}{R}\right]} \quad \text{(Equation 1)}$$

Here, p represents the density of the liquid contained in the container 200, R represents the radius of the generated bubble, P represents an atmospheric pressure, and a represents surface tension of the liquid. That is, the resonance frequency of the bubble represents the size of the bubble or characteristics of the bubble according to a property of the liquid or the like. Thus, it will be understood that as the size of the bubble or the like increases, the resonance frequency of the bubble decreases, as shown in Equation 1 below.

As illustrated in FIG. 1, in the bubble volume control apparatus 1 according to the present invention, the ultrasonic generator 100 provided just above a surface of the liquid contained in the container 200 may emit a pressure wave $p_s$ of a sinusoidal shape, which is expressed below, to be transmitted to the bubble located at the bottom of the container 200 via the liquid as a medium.

$$Ps = P + a*\sin(2\pi*f*t) \quad \text{(Equation 2)}$$

Here, a represents the amplitude of the ultrasonic wave, f represents the frequency of the ultrasonic wave, and t represents time.

In this case, the wavelength λ of the ultrasonic wave is defined as λ=c/f, wherein c represents the velocity of sound in the liquid L contained as a medium in the container 200.

An amplitude of a plane pressure wave Ps emitted by the ultrasonic generator 100 is largest at a wavelength λ/4 according to the shape of a sine wave periodic function. On the other hand, a wavelength of a spherical wave having a largest amplitude may be λ/2.

Accordingly, if a liquid surface height H to which the ultrasonic wave generated by the ultrasonic generator 100 is transmitted, i.e., a distance from the ultrasonic generator 100 to the bottom of the container 200 to which the ultrasonic wave having the wavelength λ travels, satisfies H=λ/4, the bubble at the bottom of the container 200 meets the ultrasonic wave which is the pressure wave Ps emitted by the ultrasonic generator 100 when an amplitude of the ultrasonic wave is largest, thereby causing multiple resonance.

Thus, a change of the pressure of the bubble may be amplified due to multiple resonance or the like and the amount of pressure applied to the bubble may be maximum, when the ultrasonic generator 100 emits the ultrasonic wave, which is the pressure wave Ps having a frequency which is the same as the resonance frequency $f_N$ of the bubble according to Equation (1) above, onto a liquid surface with a height H(=λ/4) corresponding to a wavelength λ of a largest amplitude.

It is noted that the volume of a bubble, such as air, located at a wall surface, i.e., the bottom, of a liquid container may be controlled to be, for example, grown, reduced, or removed, based on the above principle.

Examples of a resonance frequency according to a size of a fine bubble and a height H of a liquid surface at which resonance is amplified according to the present invention are as shown in Table 1 below.

It was experimentally found that a range in which a bubble volume control method according to the present invention is applicable is effective under the following conditions.

First, the effects of the present invention were proved when the size of a bubble such as fine air was in a range of 1 μm to 100 μm, an amplitude of pressure of a pressure wave Ps emitted by an ultrasonic generator was in a range of 1.013 kPa to 10.13 kPa, a frequency of an ultrasonic wave generated by the ultrasonic generator to match a resonance frequency according to the size of the bubble was in a range of 33 kHz to 4745 kHz, and a liquid surface height H satisfying a multiple resonance condition was in a range of 81 kHz to 11647 μm. The volume of the bubble was controlled to some extent even when the radius of the bubble, the resonance frequency, or the liquid surface height H was beyond the above ranges, but it is desirable to adjust parameters to satisfy the above ranges in order to obtain a remarkable effect.

As shown in Table 1 below, the resonance frequency $f_N$ is inversely proportional to the radius R of the bubble and is proportional to the liquid surface height H. When conditions of the radius R of the bubble, the resonance frequency $f_N$, and the liquid surface height H with respect to the bubble are determined in combinations as shown in Table 1 below, a function of controlling the volume of the bubble using a pressure wave Ps due to multiple resonance may be maximized.

TABLE 1

| R (μm) | $F_N$ (kHz) | H (μm) |
|---|---|---|
| 1 | $4.745 \times 10^3$ | $8.113 \times 10^1$ |
| 2 | $2.041 \times 10^3$ | $1.886 \times 10^2$ |
| 5 | $7.252 \times 10^2$ | $5.308 \times 10^2$ |
| 7.5 | $4.689 \times 10^2$ | $8.209 \times 10^2$ |
| 10 | $3.461 \times 10^2$ | $1.112 \times 10^3$ |
| 20 | $1.687 \times 10^2$ | $2.281 \times 10^3$ |
| 50 | $6.646 \times 10^1$ | $5.792 \times 10^3$ |
| 75 | $4.415 \times 10^1$ | $8.719 \times 10^3$ |
| 100 | $3.305 \times 10^1$ | $1.164 \times 10^4$ |

A result of a test according to an embodiment of the present invention will be described in detail with reference to FIGS. 2 to 4 below.

Conditions of the test will be described in detail below. A pressure a of an amplitude of an ultrasonic wave which is a pressure wave Ps was 2.026 kpa, an ultrasonic generator emitting a sinusoidal plane wave having a frequency f=725 kHz (in the case of water vapor, the frequency varies according to a specific heat ratio γ) equal to a natural frequency $f_N$ of an underwater air bubble was provided on a liquid surface, and a container with a height H=531 μm corresponding to λ/4 of the plane wave (having a wavelength λ of 2,124 μm) at which an amplitude was largest was filled with water and an air bubble with a radius of 5 μm was generated at the bottom of the container.

Figure 2:
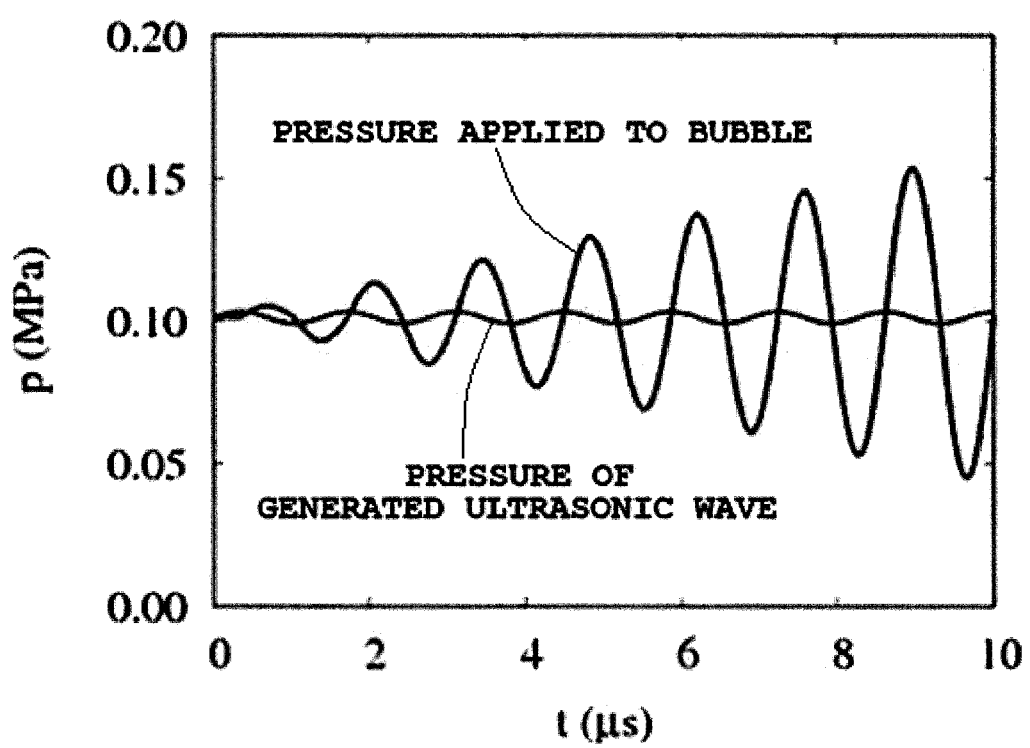
FIG. 2 illustrates a variation in a pressure of a liquid contained in a liquid container versus a position when an ultrasonic wave was generated on a surface of the liquid.

FIG. 2 illustrates a variation in a pressure of a liquid contained in a liquid container versus a position of a bubble when an ultrasonic wave was generated on a surface of the liquid.

A pressure wave Ps emitted by an ultrasonic generator has a repetitive sinusoidal shape as indicated by a blue solid line graph.

The pressure wave Ps transmitted via a medium (a liquid such as water) arrived at a bubble located at the bottom of a container, and the amount of pressure of the liquid increased with time due to an effect the height of the container and characteristics of the water when compressed, as indicated by a red solid line graph.

That is, it was found that, when the radius of the bubble, the frequency of the ultrasonic wave, and the heights of the bubble and a liquid surface were appropriately combined, the volume of the bubble was controlled by pressurizing the bubble by emitting the ultrasonic wave onto the liquid as a medium to transmit the pressure wave Ps of a sinusoidal shape of which the size increases with time as indicated by the red solid line graph of FIG. 2 to the bubble located at the bottom of the container containing the liquid. That is, the volume of the bubble may be gradually reduced during an operation period in which the operation of the ultrasonic generator 100 is maintained, and be gradually recovered to its original size in a non-operation period in which the generation of the ultrasonic wave was stopped. Thus, the original size of the bubble may be reduced to be within a certain range and the reduced volume of the bubble may be maintained to be within a desired range by appropriately combining the operation period and the non-operation period of the ultrasonic generator 100.

In other words, because the size of the pressure wave Ps increases with time, the present invention is distinguished from the techniques introduced in the past. The existing studies have been conducted to try to seek various uses of bubbles, based on an assumption that the sizes of the bubbles are adjustable, but a method of controlling the volume of bubbles, and particularly, the relationship among the size of the bubbles, a frequency of an ultrasonic wave, a wavelength, and a liquid surface height, etc. has not been investigated. However, the volume of a bubble can be actively controlled under the above conditions.

Figure 3:
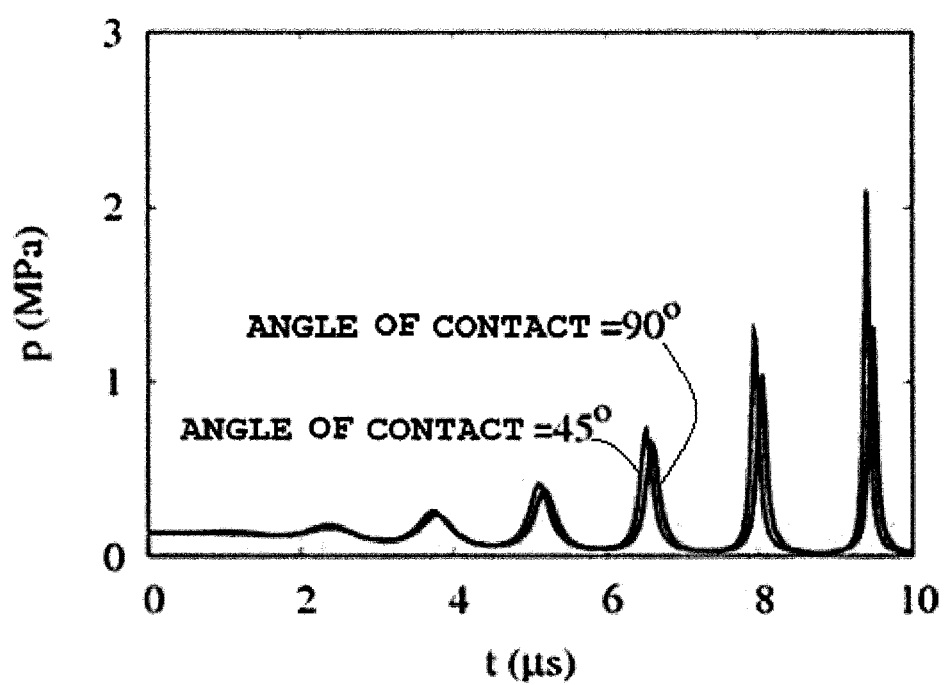
FIG. 3 illustrates a variation in a pressure versus an angle of contact between a bubble and the bottom of a liquid container.

FIG. 3 illustrates a variation in a pressure versus an angle of contact between a bubble and the bottom of a liquid container.

A pressure of the bottom of a container at which a bubble was located was sharply changed due to resonance produced by an ultrasonic wave and the bubble and multiple resonance produced when the resonance was amplified due to an effect of the height of the container, achieved by taking into account a wavelength corresponding to a largest amplitude.

As time went by, a liquid contained in the container was more sharply pressurized from 1 Mpa to 2 Mpa than when there was no bubble (as indicated by the red solid line in FIG. 2), thereby causing a behavior (growth, contraction, or removal) of the bubble due to the change of the pressure.

Furthermore, an effect of compressing a liquid contained in the container through the growth, contraction, or removal of the bubble was increased and thus was more pressurized over time, as the angle of contact between the bottom of the container and the bubble became smaller.

Accordingly, it is expected that the bubble may be formed to be relatively flat in order to control a responsiveness of control of the volume of a bubble or a bubble volume change ratio volume, or control performance when a change of the volume of the bubble is needed will be maximized by pre-pressurizing the bubble using an ultrasonic wave.

Figure 4:
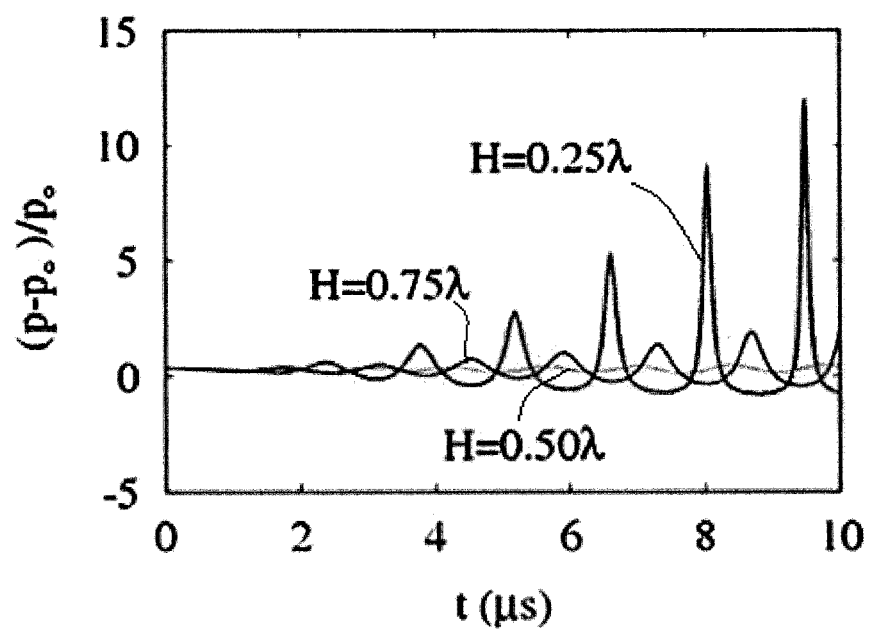
FIG. 4 illustrates a variation in a ratio of increase in a pressure applied to a bubble to an atmospheric pressure according to a liquid surface height of a liquid container over time.

FIG. 4 illustrates a variation in a ratio of increase in a pressure applied to a bubble to an atmospheric pressure according to a liquid surface height of a liquid container over time.

The size of a pressure wave Ps was not greatly changed over time when a condition of maximizing the resonance effect, i.e., $H=\lambda/4$, according to an embodiment was not satisfied, i.e., in an experiment indicated by a blue solid line, in which a frequency of an ultrasonic wave was set to match a radius of a bubble according to Equation (1) above and a liquid surface height was set to about 75% of a wavelength of the ultrasonic wave (i.e., $H=0.75\lambda$) and an experiment indicated by a green solid line, in which a liquid surface height was set to about 50% of a wavelength of the ultrasonic wave (i.e., $H=0.50\lambda$), even when a frequency of the ultrasonic wave satisfied a multiple resonance condition according to the size of a bubble.

That is, the volume of the bubble did not change to a large extent over time.

In contrast, in an experiment indicated by a red solid line, in which a liquid surface height was set to about 25% of a wavelength of an ultrasonic wave, i.e., a quarter of the wavelength $\lambda$ of the ultrasonic wave (i.e., $H=0.25\lambda$), a size of a pressure wave Ps was sharply increased with time due to a resonance phenomenon, thereby maximizing a function of controlling the volume of a bubble.

While the present invention has been described above with respect to exemplary embodiments thereof, it would be understood by those of ordinary skilled in the art that various changes and modifications may be made without departing from the technical conception and scope of the present invention defined in the following claims. Thus, it is clear that all modifications are included in the technical scope of the present invention as long as they include the components as claimed in the claims of the present invention.

The invention claimed is:

1. A bubble volume control method comprising, when there is a bubble of a radius R at the bottom of a container containing a liquid of a density p and a specific heat ratio γ, controlling volume of the bubble to be reduced by emitting an ultrasonic wave having a resonance frequency $f_N$ toward the bubble through an ultrasonic generator provided above a surface of the liquid to pressurize the bubble, wherein the resonance frequency $f_N$ is defined by:

$$f_N = \frac{1}{2\pi}\sqrt{\frac{1}{\rho R^2}\left[3\gamma p_o + 2(3\gamma-1)\frac{\sigma}{R}\right]},$$

wherein p represents the density of the liquid contained in the container, R represents the radius of the bubble, Po represents an atmospheric pressure, and σ represents surface tension of the liquid.

2. The bubble volume control method of claim 1, wherein the ultrasonic generator pressurizes the bubble by transmitting a pressure wave Ps of a sinusoidal shape to the bubble through the liquid as a medium, wherein the pressure wave Ps is defined by:

$$Ps=P+a*\sin(2\pi*f*t),$$

wherein a represents an amplitude of the ultrasonic wave, f represents a frequency of the ultrasonic wave, and t represents time.

3. The bubble volume control method of claim 2, wherein the bubble is located at the bottom of the container, and a height H from the bubble to the surface of the liquid is ¼ of a wavelength λ of the ultrasonic wave.

4. The bubble volume control method of claim 1, wherein the ultrasonic generator transmits a pressure wave Ps of a sinusoidal shape to the bubble.

5. The bubble volume control method of claim 4, wherein the bubble is located at the bottom of the container, and a height H from the bubble to the surface of the liquid is ½ of a wavelength λ of the ultrasonic wave.

6. The bubble volume control method of claim 1, wherein, when an operation of the ultrasonic generator is stopped, pressure applied to the bubble is removed and thus the volume of the bubble is restored to its original volume.

7. The bubble volume control method of claim 6, wherein the volume of the bubble is controlled to be within a predetermined range by repeating an operation period in which the ultrasonic generator is operated and a non-operation period in which the operation of the ultrasonic generator is stopped.

8. The bubble volume control method of claim 1, wherein the radius of the bubble of which the volume is controlled by the ultrasonic wave generated by the ultrasonic generator is in a range of 1 μm to 100 μm.

9. The bubble volume control method of claim 2, wherein a pressure of an amplitude of the pressure wave Ps is in a range of 1.013 kPa to 10.13 kPa.

10. The bubble volume control method of claim 1, wherein the resonance frequency $f_N$ is in a range of 33 kHz to 4745 kHz.

11. The bubble volume control method of claim 3, wherein the height H of the surface of the liquid is in a range of 81 μm to 11647 μm.

12. The bubble volume control method of claim 1, wherein the radius of the bubble is inversely proportional to the resonance frequency $f_N$ of the ultrasonic wave generated by the ultrasonic generator, and is proportional to the height H of the surface of the liquid.

13. The bubble volume control method of claim 4, wherein a pressure of an amplitude of the pressure wave Ps is in a range of 1.013 kPa to 10.13 kPa.

14. The bubble volume control method of claim 5, wherein the height H of the surface of the liquid is in a range of 81 μm to 11647 μm.

15. A bubble volume control apparatus comprising:
an ultrasonic generator; and
a liquid container,
wherein a liquid of a density p and a specific heat ratio γ is contained in the liquid container,
the ultrasonic generator emits an ultrasonic wave toward a surface of the liquid in the liquid container, and
when a radius of a bubble at the bottom of the liquid container is R, the ultrasonic generator generates an ultrasonic wave having a resonance frequency $f_N$ to pressurize the bubble to reduce the volume of the bubble, wherein the resonance frequency is defined by:

$$f_N = \frac{1}{2\pi}\sqrt{\frac{1}{\rho R^2}\left[3\gamma p_o + 2(3\gamma - 1)\frac{\sigma}{R}\right]},$$

wherein p represents the density of the liquid contained in the container, R represents the radius of the bubble, Po represents an atmospheric pressure, and σ represents surface tension of the liquid.

16. The bubble volume control apparatus of claim 15, wherein the ultrasonic wave generated by the ultrasonic generator comprises a plane wave of a sinusoidal shape, and a liquid surface height of the liquid contained in the liquid container is ¼ of a wavelength λ of the ultrasonic wave having the resonance frequency $f_N$ and generated by the ultrasonic generator from the bottom of the liquid container.

* * * * *